United States Patent [19]

Pitner et al.

[11] Patent Number: 6,114,518

[45] Date of Patent: Sep. 5, 2000

[54] SYNTHESIS AND USE OF LABELLED PHOSPHORAMIDITE COMPOSITIONS

[75] Inventors: J. Bruce Pitner; C. Preston Linn, both of Durham, N.C.

[73] Assignee: Becton, Dickinson and Company, Franklin Lakes, N.J.

[21] Appl. No.: 09/409,471

[22] Filed: Sep. 30, 1999

[51] Int. Cl.[7] .......................... C07H 19/00; C07H 21/00; C07H 21/02; C07H 21/04; C07H 19/04

[52] U.S. Cl. ............................ 536/25.3; 435/6; 536/22.1; 536/23.1; 536/24.3; 536/25.3; 536/25.33; 536/25.34; 536/26.22

[58] Field of Search ................................ 435/6; 536/22.1, 536/23.1, 24.3, 25.3, 25.32, 25.33, 25.34, 26.22

[56] References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |
| 4,725,677 | 2/1988 | Koster et al. | 536/27 |
| 5,380,880 | 1/1995 | Pitner et al. | 549/394 |
| 5,512,667 | 4/1996 | Reed et al. | 536/24.31 |
| 5,608,046 | 3/1997 | Cook et al. | 536/23.1 |
| 5,648,211 | 7/1997 | Fraiser et al. | 435/6 |
| 5,677,437 | 10/1997 | Teng et al. | 536/23.1 |
| 5,688,941 | 11/1997 | Cook et al. | 536/25.3 |
| 5,691,145 | 11/1997 | Pitner et al. | 435/6 |
| 5,721,355 | 2/1998 | Brush | 536/25.32 |
| 5,952,202 | 9/1999 | Aoyagi et al. | 435/91.2 |

OTHER PUBLICATIONS

1999 Catalog: Glen Research Products for DNA Research Glen Research Product Information, www.glenres.com/productfiles/10–5912.html.

*Primary Examiner*—Jezia Riley
*Attorney, Agent, or Firm*—Donna R. Fugit

[57] ABSTRACT

The present invention provides labelled phosphoramidite compositions, methods for making these labelled phosphoramidite compositions, and methods for using these labelled phosphoramidite compositions for labelling oligonucleotides. Even more particularly, the present invention provides compositions and methods for labeling the 5' end of oligonucleotides during synthesis of the oligonucleotides.

22 Claims, No Drawings

SYNTHESIS AND USE OF LABELLED PHOSPHORAMIDITE COMPOSITIONS

FIELD OF THE PRESENT INVENTION

The present invention relates to novel labelled phosphoramidite compositions, methods of making these compositions, and methods of using these compositions to label nucleic acids, especially oligonucleotides. Oligonucleotides labelled with the compositions of the present invention are used in hybridizing to target nucleotides and may be used for detection, localization and measurement of target nucleotides.

BACKGROUND OF THE INVENTION

Labelling of nucleic acids and/or oligonucleotides, with reporter molecules is important in many areas of chemical and biological research. Due to the fact that single stranded oligonucleotides hybridize with complementary single or double stranded oligonucleotides, labelled oligonucleotides can be used as probes in cloning procedures, blotting procedures such as Northern blot analysis, and in situ hybridization procedures. Additionally, labelled oligonucleotides can be used in conjunction with oligonucleotide amplification procedures such as the Polymerase Chain Reaction (PCR), Strand Displacement Amplification (SDA), Nucleic Acid Sequence-Based Amplification (NASBA), and Ligase Chain Reaction (LCR) to detect the presence of amplified oligonucleotides. Thus, labelled oligonucleotides are used for both qualitative and quantitative analyses of target nucleic acid molecules.

Oligonucleotides can be labelled with several different types of reporter molecules. For example, oligonucleotides can be labelled with radioisotopes such as $^{32}P$, $^{3}H$, $^{14}C$, $^{35}S$, $^{125}I$, or $^{131}I$. Oligonucleotides may also be labelled with non-isotopic labels such as fluorescein, biotin, digoxigenin, and alkaline phosphatase. However, when using labelled oligonucleotides for the identification and quantification of target nucleic acids, fluorescent labels have been favored as they provide a sensitive, non-radioactive means for the detection of probe hybridization. The fluorescent labels may be used alone, or in conjunction with quenching dyes in fluorescence energy transfer reactions. Fluorescence energy transfer occurs between a donor fluorophore and an acceptor or quenching dye when the absorption spectrum of the acceptor dye overlaps the emission spectrum of the donor fluorophore, and the two dyes are in close proximity. Upon excitation of the donor molecule, for example with ultraviolet energy, the energy emitted from the donor molecule is transferred to the neighboring acceptor molecule which accepts and quenches this energy. This acceptance of the energy by the acceptor results in quenching of donor fluorescence. The overall effect of such energy transfer is that the emission of the donor is not detected until the donor and acceptor are separated, for example upon hybridization of a labeled probe to a target nucleotide.

In practice, the donor and acceptor molecules may either reside on complementary oligonucleotides or on a single oligonucleotide. When incorporated into complementary oligonucleotides, quenching occurs upon hybridization of the separately labelled oligonucleotides. In contrast, when the donor and acceptor are linked to a single oligonucleotide, hybridization to the target oligonucleotide usually results in reduced quenching due to an increased distance between the donor and acceptor which decreases the effect of energy transfer. Reduced quenching is observed as increased ability to detect the energy emitted from the donor. For example, an acceptor and donor may be linked to the ends of a self-complementary oligonucleotide such that under non-hybridizing conditions a hairpin is formed which brings the acceptor and donor into close proximity and causes quenching. Hybridization of the self-complementary oligonucleotide results in linearization of the hairpin and reduced quenching. Additionally, to further contribute to the change in fluorescence upon hybridization, a restriction endonuclease site may be placed between the acceptor and donor dyes such that the site is only cleavable in the presence of target binding.

Two of the quenching or acceptor molecules that are used with the detection techniques described above are DABSYL and DABCYL. The term "DABSYL" refers to a 4-dimethylaminophenylazo-benzenesulfonyl acid while the term "DABCYL" refers to a 4-dimethylaminophenylazo-benzene-4'-carbonyl structure. The term "DABCYL thioamide" refers to a 4-dimethylaminophenylazophenyl-4'-isothiocyanate. These molecules have absorption spectra that overlap the emission spectrum of donor molecules such as EDANS, BODIPY dyes, fluorescein, tetramethylrhodamine, Texas Red, rhodamine-X, Cy3 and Cy5. DABCYL, DABSYL and DABCYL thioamide are non-fluorescent chromophores, and therefore provide an advantage over other quenchers since they do not fluoresce when exposed to emission from the donor molecule or to the excitation wavelengths used to excite the donor.

Several reagents have been produced for linking acceptor dyes, such as DABCYL, to oligonucleotides. For example, Glen Research makes a 3'-DABCYL CPG 500 product that allows linkage of the DABCYL molecule to the 3' end of an oligonucleotide (1998 Catalog, Glen Research, Sterling, Va.). One drawback to this product however, is that the DABCYL molecule cannot be linked to the interior of the oligonucleotide chain nor to the 5' end of the oligonucleotide chain. Another product, DABCYL-cdT, facilitates linkage of the DABCYL molecule to the internal nucleotides of a growing oligonucleotide chain, but is limited in application to the nucleotides thymidine and uridine (Glen Research).

Derivatives of DABSYL-type reactive dyes present problems in post-labeling of oligonucleotides due to their high hydrophobicity and low aqueous solubility. These characteristics require the coupling reaction with 5'-amino-linked DNA or RNA to be performed in buffers with a high percentage of dimethylsulfoxide (DMSO) or dimethylformamide (DMF) and complicates purification of labeled DNA or RNA from dye by-products.

Accordingly, what is needed are labelled compositions that may be used as reagents during oligonucleotide synthesis for the linkage of labels, such as acceptor dyes, to the 5' end of oligonucleotides. Also needed are labelled compositions, capable of linking to the 5' end of oligonucleotides, which are less hydrophobic than labelled compositions taught in the prior art. What is also needed are methods for labelling oligonucleotides that reduce or eliminate the problems inherent in prior art methods such as the use of hydrophobic solvents and hydrophobic buffers that complicate purification of the labelled oligonucleotides.

SUMMARY OF THE INVENTION

The present invention provides novel reagents comprising labelled phosphoramidite compositions, methods of making these compositions, and methods of using these compositions for labelling oligonucleotides. In a preferred embodiment, the labelled phosphoramidite compositions are labelled with acceptor dyes. These acceptor dyes include, but are not limited to DABCYL, DABSYL and DABCYL thioamide.

These labelled phosphoramidite compositions are generally described by the following generic structure:

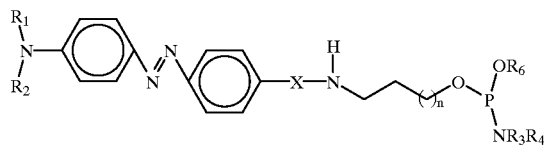

wherein X is $SO_2$, CO, or CS; $R_1$ and $R_2$ are the same or different and are an alkyl group from 1 to 6 carbons in length or can jointly form with the nitrogen to which they are bound a 5 or 6-membered cyclic ring, the ring optionally containing oxygen; $R_3$ and $R_4$ are the same or different and are either isopropyl or other alkyl group; $R_6$ may be $(CH_2)_2CN$ or $CH_3$; and n is an integer from 1 to 10 which represents the length of the hydrocarbon chain $(CH_2)_n$, which links to the phosphoramidite.

The labelled phosphoramidite compositions of the present invention may be added to the 5' end of oligonucleotides during synthesis of the oligonucleotide. Because the labelled phosphoramidite compositions are not already attached to a specific nucleotide base, they can be linked to any base at the 5' end of the growing oligonucleotide chain.

Oligonucleotides labelled with the labelled phosphoramidite compositions of the present invention are useful as probes in a variety of applications such as energy transfer probes for detection of nucleic acids. The DABSYL, DABCYL and DABCYL thioamide moieties are excellent quenchers in the fluorescence energy transfer process since they are non-fluorescent chromophores, and thus do not interfere with detection of the emission from the donor molecule as many fluorescent quenchers do. In a specific embodiment, the labelled oligonucleotides may be used in nucleic acid amplification techniques for detection of nucleic acids.

Accordingly, an object of the present invention is to provide labelled phosphoramidite compositions.

More specifically, it is an object of the present invention to provide labelled phosphoramidite compositions wherein DABSYL, DABCYL or DABCYL thioamide is the label.

A specific object of the present invention is to provide the labelled phosphoramidite composition represented by the following structure.

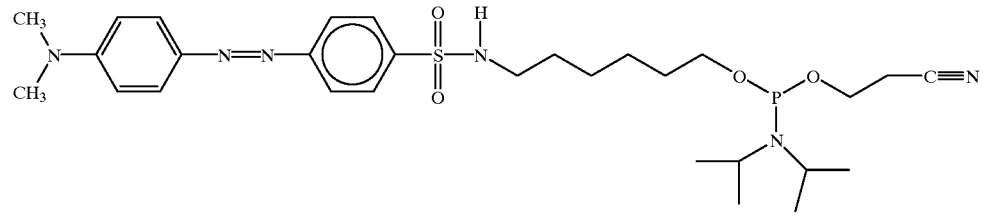

Another specific object of the present invention is to provide the labelled phosphoramidite composition represented by the following structure.

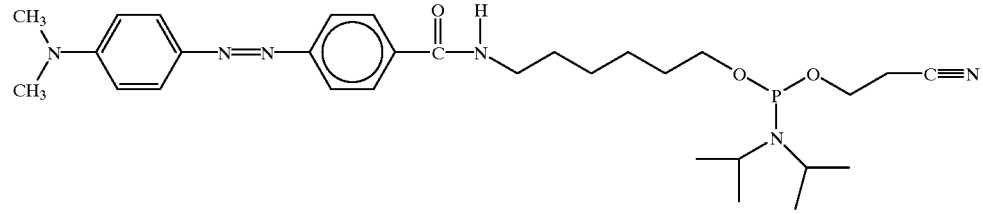

Another specific object of the present invention is to provide the labelled phosphoramidite composition represented by the following structure.

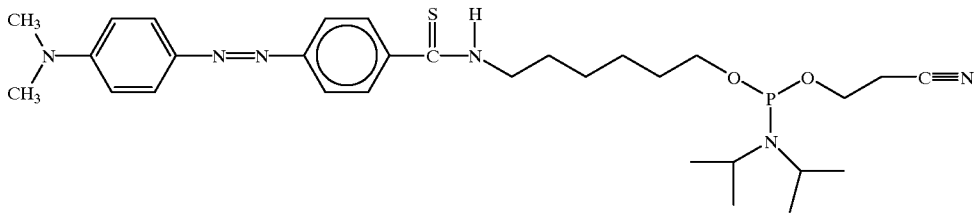

Another object of the present invention is to provide methods of synthesizing labelled phosphoramidite compositions.

Still another object of the present invention is to provide methods of synthesizing phosphoramidite compositions labelled with DABCYL, DABSYL or DABCYL thioamide, wherein these labelled phosphoramidite compositions are useful for labelling the 5' end of oligonucleotides.

It is also an object of the present invention to provide methods of using the labelled phosphoramidite compositions, for example in methods for labeling oligonucleotides to be used as probes for detecting target nucleic acids.

Another object of the present invention is to provide methods for 5' labelling of oligonucleotides with labelled phosphoramidite compositions.

A specific object of the present invention is to provide methods for 5' labelling of oligonucleotides with DABCYL, DABSYL or DABCYL thioamide labelled phosphoramidite compositions.

These and other objects, features and advantages of the present invention will become apparent after a review of the following detailed description.

DETAILED DESCRIPTION OF THE PREFERRED EMBODIMENTS

Compositions comprising labelled phosphoramidite compositions, methods for making these compositions, and methods for using these compositions to label oligonucleotides are provided in the present invention. As used herein, the term labeled phosphoramidite composition refers to those molecules containing at least a 4-dialkylaminophenylazo-benzene structure linked to a phosphoramidite structure.

Phosphoramidites are known to those skilled in the art of nucleic acid chemistry and are characterized generally by the following structures:

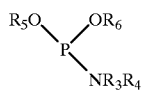

wherein $R_3$ and $R_4$ are the same or different, and are either isopropyl or other alkyl group such as methyl, ethyl, propyl, butyl, pentyl, hexyl, heptyl, octyl, nonyl and heptyl. In a preferred embodiment, $R_3$ and R4 are the same or different, and are isopropyl, and $R_6$ is $(CH_2)_2CN$. $R_5$ represents the attachment point to a 5' end of a nucleoside. $R_6$ may be $(CH_2)_2CN$ or $CH_3$.

The term "alkyl" is commonly known to one of skill in the art as referring to an aliphatic hydrocarbon structural subunit of the general formula $C_nH_{2n+1}$. Examples of alkyls include methyl, ethyl, propyl, butyl, pentyl, hexyl, heptyl, octyl, nonyl and heptyl. Definitions for other terms used herein are as follows. "Oligonucleotide," as used herein, refers to a oligodeoxyribonucleotide (DNA) or oligoribonucleotide (RNA) in either single-stranded or double-stranded form, and unless otherwise limited, encompasses analogs of natural nucleotides. The term "oligonucleotide", as used herein includes 2'-amino and 2'-methoxy ribonucleotides. By the term "probe" is meant a nucleic acid sequence that can be used for selective hybridization with complementary nucleic acid sequences. The terms "probe" or "probes" as used herein are defined to include "primers."

Generic Structure of the Labelled Phosphoramidite Compositions

The labelled phosphoramidite compositions of the present invention are defined by the generic formula:

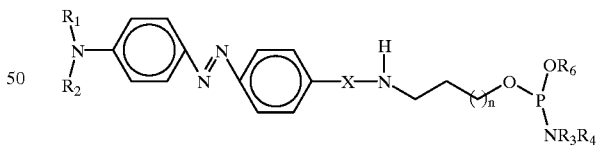

wherein X is $SO_2$, C=O or C=S; $R_1$ and $R_2$ are the same or different and are an alkyl group from 1 to 6 carbons or can jointly form with N a 5 or 6-membered heterocyclic ring, the ring optionally containing oxygen, as shown below; $R_3$ and $R_4$ are the same or different and are either isopropyl or other alkyl group; and n is an integer from 1 to 10 which represents the length of the hydrocarbon chain which links to the modified phosphoramidite structure. $R_3$ and $R_4$ may be the same or different and may be methyl, ethyl, propyl, butyl, pentyl, hexyl, heptyl, octyl, nonyl or heptyl. $R_6$ may be $(CH_2)_2CN$ or $CH_3$.

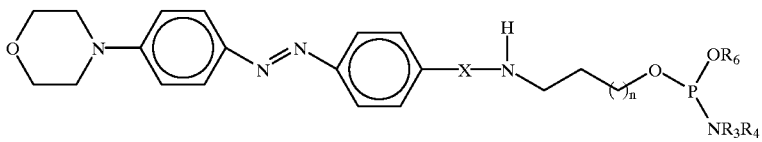

Preferred sub-generic structures include the following structures:

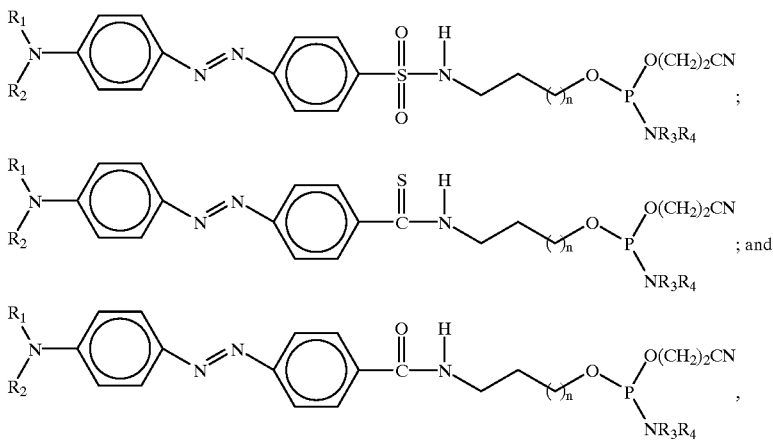

wherein $R_1$ and $R_2$ are the same or different and are an alkyl group from 1 to 6 carbons in length or can jointly form with the nitrogen to which they are bound a 5 or 6-membered heterocyclic ring, the ring optionally containing oxygen; $R_3$ and $R_4$ are the same or different and are either isopropyl or other alkyl group; and n is an integer from 1 to 10 which represents the length of the hydrocarbon chain $(CH_2)_n$, which links to the phosphoramidite.

When X is $SO_2$, the 4-dialkylaminophenylazo-benzene-4'-sulfonyl structure is a product of sulfonyl chlorides, with appropriate aminoalkyl alcohol intermediates. When X is CO, the 4-dialkylaminophenylazo-benzene-4'-carbonyl structure is a product of reactive esters or acid chlorides, with appropriate aminoalkyl alcohol intermediates. When X is CS, the 4-dialkylaminoalkyl phenylazo-benzene-4'-thiocarbonyl structure is a product of isothiocyanates, with appropriate aminoalkyl intermediates.

The groups $R_1$ and $R_2$ are the same or different and are an alkyl group from 1 to 6 carbons, or can jointly form a 5 or 6-membered heterocyclic ring with N, the ring optionally containing oxygen. When $R_1$ and $R_2$ can jointly form a 5 or 6-membered cyclic ring with N, $NR_1R_2$ together represent N-substituted pyrrolidines, piperidines or morpholines. In the case when $R_1$ and $R_2$ do not jointly form with N a 5 or 6-membered heterocyclic ring, $R_1$ and $R_2$ may be the same or different and may be methyl, ethyl, propyl, butyl, pentyl, or hexyl. Preferred alkyl groups for $R_1$ and $R_2$ are methyl or ethyl.

The groups $R_3$ and $R_4$ are the same or different and are either isopropyl or another alkyl group including but not limited to methyl, ethyl, propyl, butyl, pentyl, hexyl, heptyl, octyl, nonyl or heptyl. In a preferred embodiment, $R_3$ and $R_4$ are isopropyl.

The length of the hydrocarbon chain $(CH_2)_n$ which links to the phosphoramidite is represented by "n," which is an integer from 1 to 10. In a preferred embodiment, n is an integer from 2 to 8. In a more preferred embodiment, n is an integer from 3 to 6. In a most preferred embodiment, n is the integer 4. It is to be understood that the hydrocarbon chain $(CH_2)_n$ may contain a double bond located in any position in the chain, or one or more functional groups which allow for linkage to other molecules. Such functional groups include, but are not limited to methyl, hydroxy, or hydroxymethyl. Through these functional groups, preferably located at carbons close to the oxygen, additional molecules may be attached, including but not limited to DABCYL, DABCYL thioamide, and DABSYL. The addition of multiple acceptor groups may increase the quenching capacity of the labelled oligonucleotides.

Two preferred subgeneric structures of the present invention are the following:

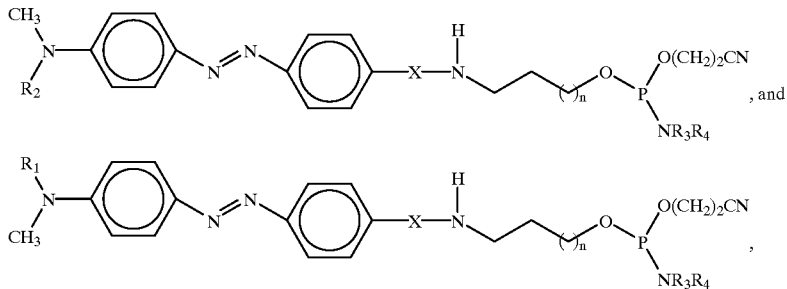

wherein X is $SO_2$, CO, or CS; $R_1$ and $R_2$ are the same or different and are an alkyl group from 1 to 6 carbons in length or can jointly form with the nitrogen to which they are bound a 5 or 6-membered heterocyclic ring, the ring optionally containing oxygen; $R_3$ and $R_4$ are the same or different and are either isopropyl or other alkyl group including but not limited to methyl, ethyl, propyl, butyl, pentyl, hexyl, heptyl, octyl, nonyl or heptyl; and n is an integer from 1 to 10 which represents the length of the hydrocarbon chain $(CH_2)_n$ which links to the phosphoramidite. In a preferred embodiment, $R_1$ and $R_2$ are the same or different and are methyl or ethyl. In a preferred embodiment, $R_3$ and $R_4$ are isopropyl.

Another preferred subgeneric structure wherein X is $SO_2$ is:

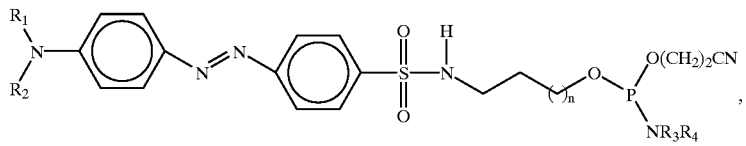

wherein $R_1$ and $R_2$ are the same or different and are an alkyl group from 1 to 6 carbons in length or can jointly form with the nitrogen to which they are bound a 5 or 6-membered heterocyclic ring, the ring optionally containing oxygen; $R_3$ and $R_4$ are the same or different and are either isopropyl or other alkyl group including but not limited to methyl, ethyl, propyl, butyl, pentyl, hexyl, heptyl, octyl, nonyl or heptyl; and n is an integer from 1 to 10 which represents the length of the hydrocarbon chain $(CH_2)_n$ which links to the phosphoramidite.

Another preferred subgeneric structure wherein X is CO is:

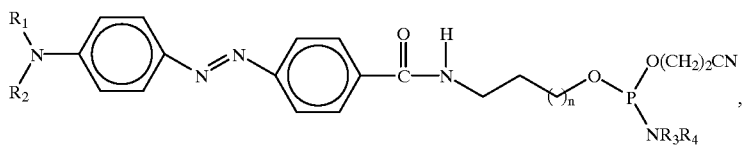

wherein $R_1$ and $R_2$ are the same or different and are an alkyl group from 1 to 6 carbons in length or can jointly form with the nitrogen to which they are bound a 5 or 6-membered cyclic ring, the ring optionally containing oxygen; $R_3$ and $R_4$ are the same or different and are either isopropyl or other alkyl group including but not limited to methyl, ethyl, propyl, butyl, pentyl, hexyl, heptyl, octyl, nonyl or heptyl; and n is an integer from 1 to 10 which represents the length of the hydrocarbon chain $(CH_2)_n$ which links to the phosphoramidite.

Yet another preferred subgeneric structure wherein X is CS is:

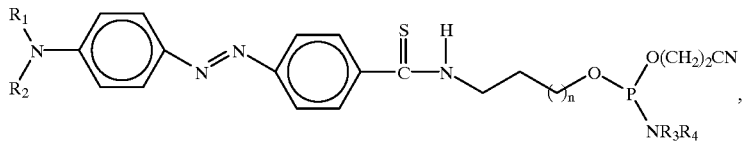

wherein $R_1$ and $R_2$ are the same or different and are an alkyl group from 1 to 6 carbons in length or can jointly form with the nitrogen to which they are bound a 5 or 6-membered heterocyclic ring, the ring optionally containing oxygen; $R_3$ and $R_4$ are the same or different and are either isopropyl or other alkyl group including but not limited to methyl, ethyl, propyl, butyl, pentyl, hexyl, heptyl, octyl, nonyl or heptyl; and n is an integer from 1 to 10 which represents the length of the hydrocarbon chain $(CH_2)_n$ which links to the phosphoramidite.

One preferred composition of the present invention is represented by the following structure wherein $R_1$ and $R_2$ are methyl, X is $SO_2$, n is 4 and $R_3$ and R4 are both isopropyl.

The labelled phosphoramidite compositions of the present invention are useful for 5' labelling of oligonucleotides. They are added to the oligonucleotide during the chemical-synthesis of the oligonucleotide, thereby eliminating problems encountered in the prior art with post-synthesis labelling.

Methods of Making Labelled Phosphoramidite Compositions

The present invention provides methods of making the labelled phosphoramidite compositions described herein. In a general manner, the labelled phosphoramidites compositions of the present invention are made by first combining a label such as an acceptor dye, including but not limited to DABSYL chloride, DABCYL or DABCYL thioamide, with

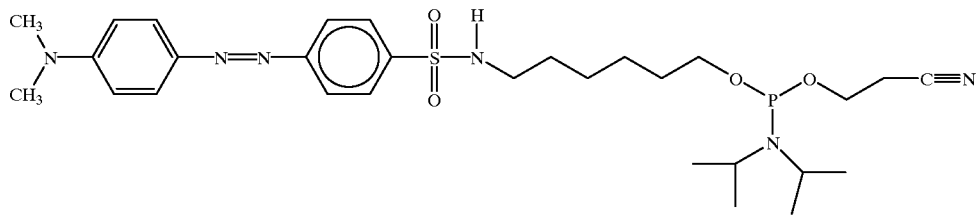

Another preferred composition of the present invention is represented by the following structure wherein $R_1$ and $R_2$ are methyl, X is CO, n is 4 and $R_3$ and $R_4$ are both isopropyl.

an amino containing alkyl alcohol to make a composition which is reactive with a phosphoramidite. The resulting composition is a phosphoramidite labelled with an acceptor

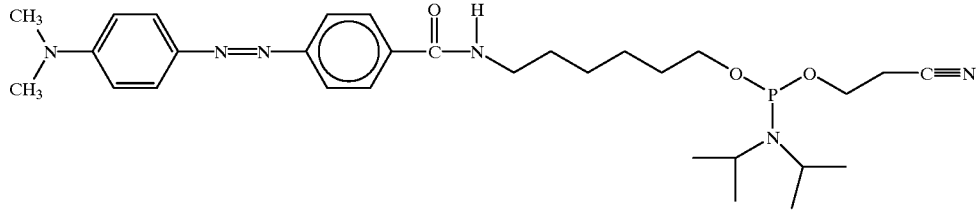

Still another preferred composition of the present invention is represented by the following structure wherein $R_1$ and $R_2$ are methyl, X is CS, n is 4 and $R_3$ and $R_4$ are both isopropyl.

dye which may be employed in the method of labelling a nucleotide at the 5' end of oligonucleotides during synthesis of the oligonucleotides.

The general reaction scheme is provided below.

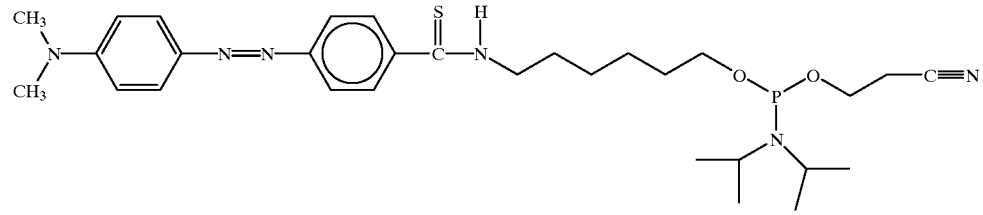

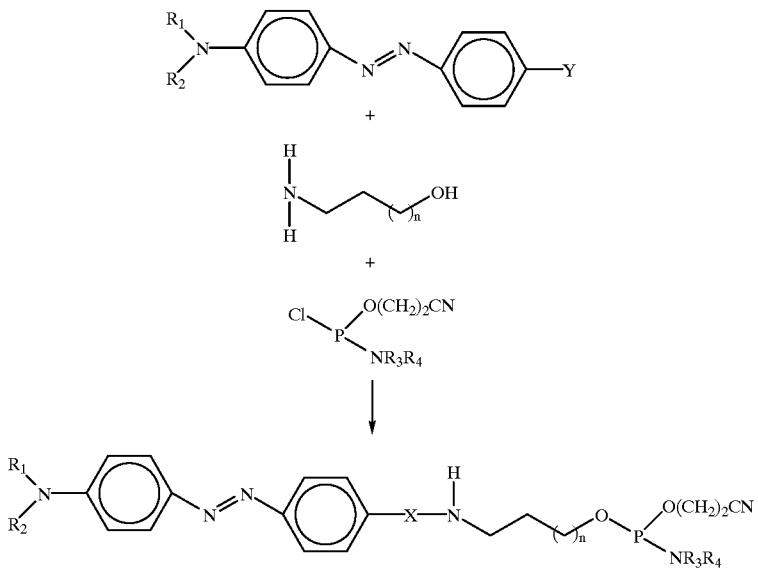

wherein Y is a reactive group such as $SO_2Cl$, COCl, active ester NHS, or SCN; X is $SO_2$, CO, or CS; $R_1$ and $R_2$ are the same or different and are an alkyl group such as methyl, ethyl, propyl, butyl, pentyl, or hexyl, or can jointly form with the nitrogen to which they are bound a 5 or 6 membered cyclic ring, the ring optionally containing oxygen; $R_3$ and R4 are the same or different and are either isopropyl or other alkyl group including, but not limited to methyl, ethyl, propyl, butyl, pentyl, hexyl, heptyl, octyl, nonyl and heptyl; and n is an integer from 1 to 10 which represents the length of the hydrocarbon chain $(CH_2)_n$ which links to the phosphoramidite and which may be optionally functionalized or contain one or more double bonds. The acceptor dyes which may be used in this reaction include, but are not limited to DABCYL, DABSYL, and DABCYL thioamide.

The amino containing alkyl alcohol generally has the formula

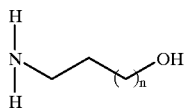

The length of the hydrocarbon chain, represented by the variable "n", may vary from 1 to 10, and preferably is from 2 to 8. In a more preferred embodiment, n is an integer from 3 to 6, and most preferably n is the integer 4. It is to be understood that the hydrocarbon chain $(CH_2)_n$ which links to the phosphoramidite may contain a double bond located in any position in the chain, or one or more functional groups, located in any position in the chain, which allow for linkage to other molecules. Such functional groups include, but are not limited to methyl, hydroxy, or hydroxymethyl. Through these functional groups, preferably located at carbon atoms close to the oxygen, additional molecules may be attached, including but not limited to DABCYL, DABCYL thioamide, and DABSYL. The addition of multiple acceptor groups may increase the quenching capacity of the labelled oligonucleotides. Dimethoxytrityl (DMT, $R_7$) may also be attached through a $CH_2$ to a carbon atom in the chain, preferably adjacent to the oxygen, as shown below.

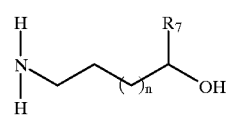

A preferred labelled phosphoramidite composition has isopropyl groups substituted for both variables $R_3$ and $R_4$ although it is to be understood that $R_3$ and $R_4$ may be the same or different and are independently either isopropyl or another alkyl group including, but not limited to methyl, ethyl, propyl, butyl, pentyl, hexyl, heptyl, octyl, nonyl and heptyl. A preferred alkyl group for either $R_3$ or $R_4$ is isopropyl. Especially preferred is a composition wherein both $R_3$ and $R_4$ are isopropyl. Also preferred are combinations of alkyl groups for $R_3$ and R4 wherein the combination is substantially non-hygroscopic and provides steric hindrance to increase stability.

Method of Synthesizing DABSYL Phosphoramidite

In one preferred form, the synthesis scheme for DABSYL phosphoramidite is set forth below.

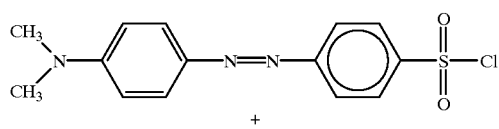

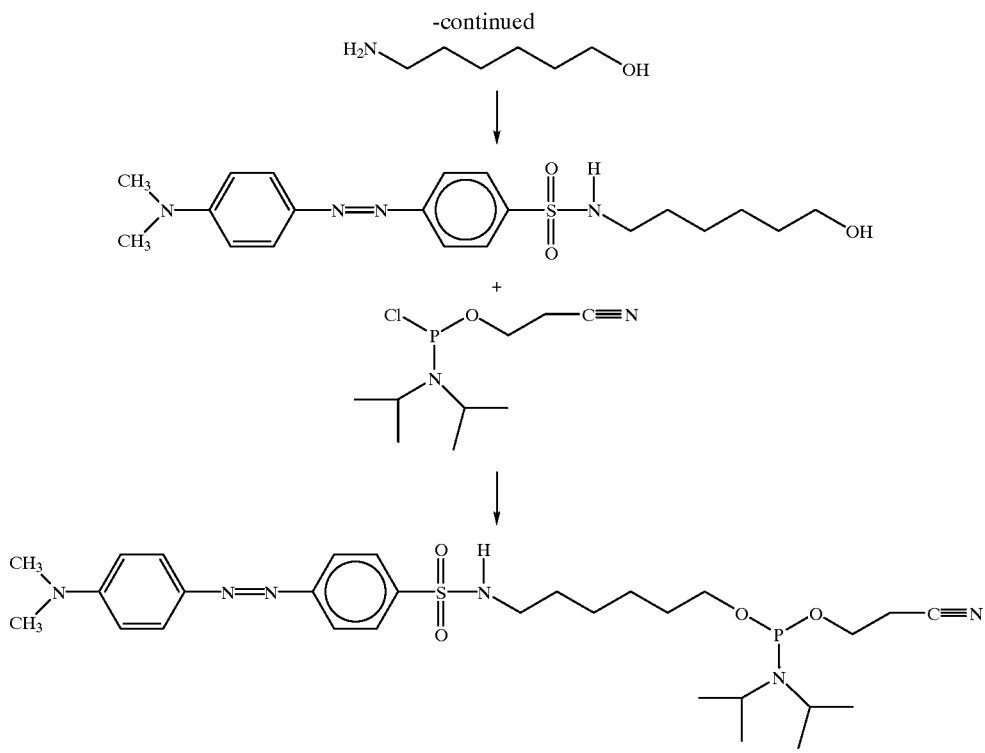

This synthesis scheme comprises the steps of first synthesizing a reaction product of DABSYL chloride and 6-aminohexanol (N-4-(4'-dimethylamino-phenyl-azo)-phenyl-sulfonyl)-6-aminohexanol), and combining the reaction product with P-chlorocyanoethyl-bis-N,N-diisopropylamino-phosphoramidite to produce DABSYL linked through a hydrocarbon chain to a phosphoramidite (DABSYL phosphoramidite; N-(4-4'-dimethylamino-phenyl-azo)-phenyl-sulfonyl)-6-aminohexanol N, N-Diisopropylchloro-β-cyanoethyl-phosphoramidite).

In general, a solution of DABSYL chloride (Fluka, about 0.2 to 20 gm) is prepared in about 0.3 to 300 mL of dry THF (Aldrich). To this solution, 6-amino-l-hexanol (Aldrich, approximately 0.1 to 10 g) is added drop-wise over approximately 1 to 100 minutes. The deep red solution is stirred under inert gas, such as argon, overnight at room temperature. Water (about 10 to 1000 mL) and a solvent, such as dichloromethane (approximately 20 to 2000 mL) are added. The aqueous phase is extracted with more dichloromethane and the combined organic fractions are dried over a hygroscopic agent, filtered, and concentrated in vacuo to give a solid. The solid is washed with a solvent system, such as ethyl acetate/hexane (20:80), and air-dried to yield about 0.2 to 20.0 gm. At this point, mass spectral data and nuclear magnetic resonance (NMR) data may be obtained on the above-described compound.

The preceding compound (approximately 8 to 800 mg) is dissolved in dry dichloromethane (about 1 to 100 mL) and stirred. Diisopropylethylamine (approximately 0.015 to 1.5 mL) is slowly added and the is mixture cooled. N,N-Diisopropylchlorophosphoramidite (about 7 to 700 mg) is added slowly as a solution in dry dichloromethane. The reaction mixture is stirred under inert gas for about 5 minutes to 5 hours with warming to room temperature. A solvent, such as methanol, (about 0.1 to 10 mL) is then added and subsequently removed by evaporation. The resulting oil is extracted several times from aqueous sodium bicarbonate with dichloromethane. The combined organic fractions are dried over a hygroscopic agent, such as $MgSO_4$, and solvent is removed. Chromatographic methods, such as flash silica gel chromatography, are used to obtain the most mobile product as an oil (0.5 to 50 mg). The NMR analysis may be performed on the resulting compound.

Method of Synthesizing DABCYL Phosphoramidite

In one preferred form, the synthesis scheme for DABCYL phosphoramidite is set forth below. This synthesis scheme comprises the steps of first synthesizing a reaction product of DABCYL chloride and 6-aminohexanol to produce N-DABCYL-6-aminohexanol, and combining the reaction product with N, N-Diisopropylchloro-β-cyanoethyl-phosphoramidite to produce DABCYL linked through a hydrocarbon chain to a phosphoramidite (DABCYL phosphoramidite; N-DABCYL-6-aminohexanol cyanoethyl phosphoramidite).

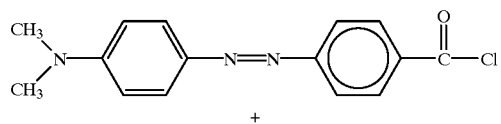

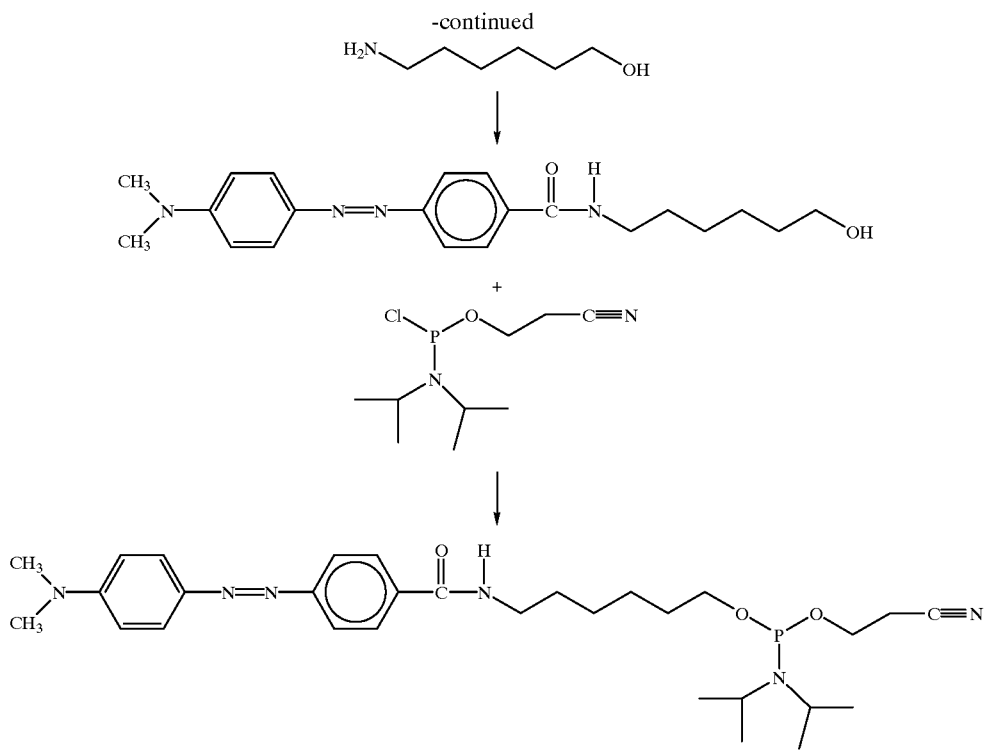

The DABCYL phosphoramidite may be prepared by reaction of 6-t-butyldimethylsilyloxyhexylamine (i.e., a protected 6-hydroxyhexylamine) with either DABCYL NHS ester or DABCYL acid chloride, followed by deprotection of the silyl group to give N-DABCYL-6-aminohexanol. This is converted to the corresponding cyanoethyl phosphoramidite by the same method as described in the second step in the DABSYL phosphoramidite synthesis recited above.

In general, a solution of DABCYL NHS ester or DABCYL acid chloride (Fluka, about 0.2 to 20 gm) is added to about 0.3 to 300 mL of dry THF (Aldrich). To this solution, 6-t-butyldimethylsilyloxyhexylamine (Aldrich, about 0.1 to 10 g) is added drop-wise over approximately 1 to 100 minutes. The solution is stirred under inert gas, preferably argon, overnight at room temperature. Water (about 10 to 1000 mL) and a solvent such as dichloromethane (approximately 20 to 2000 mL) are added. The aqueous phase is extracted with more dichloromethane and the combined organic fractions are dried over a hygroscopic agent, filtered, and concentrated in vacuo to give a solid. The solid is washed with solvent, for example, ethyl acetate/hexane (20:80), and air-dried. Chromatographic techniques, including but not limited to thin layer chromatography (TLC), silica gel chromatography, and HPLC, may be employed to analyze purity of the product. At this point, mass spectral data and nuclear magnetic resonance (NMR) data may be obtained on the above-described compound.

The preceding compound (approximately 8 to 800 mg) is dissolved in dry dichloromethane (approximately 1 to 100 mL) and stirred. Diisopropylethylamine (about 0.015 to 1.5 mL) is added by syringe and the mixture is cooled. N,N-Diisopropylchlorophosphoramidite (about 7 to 700 mg) is added slowly as a solution in dry dichloromethane. The reaction mixture is stirred under inert gas for about 5 minutes to 5 hours with warming to room temperature. A solvent, such as methanol, (about 0.1 to 10 mL) is added. The solvent is then removed by evaporation. The resulting oil is extracted several times from aqueous sodium bicarbonate with dichloromethane. The combined organic fractions are dried over a hygroscopic agent and solvent is removed. Chromatographic methods, such as flash silica gel chromatography is used to obtain the most mobile product as an oil (0.5 to 50 mg). An NMR analysis may be performed on the product.

Method of Synthesizing DABCYL Thioamide Phosphoramidite

In one preferred form, the synthesis scheme for DABCYL thioamide phosphoramidite is set forth below.

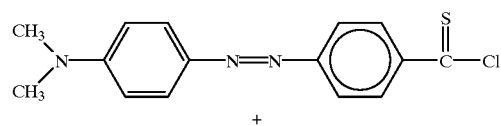

+

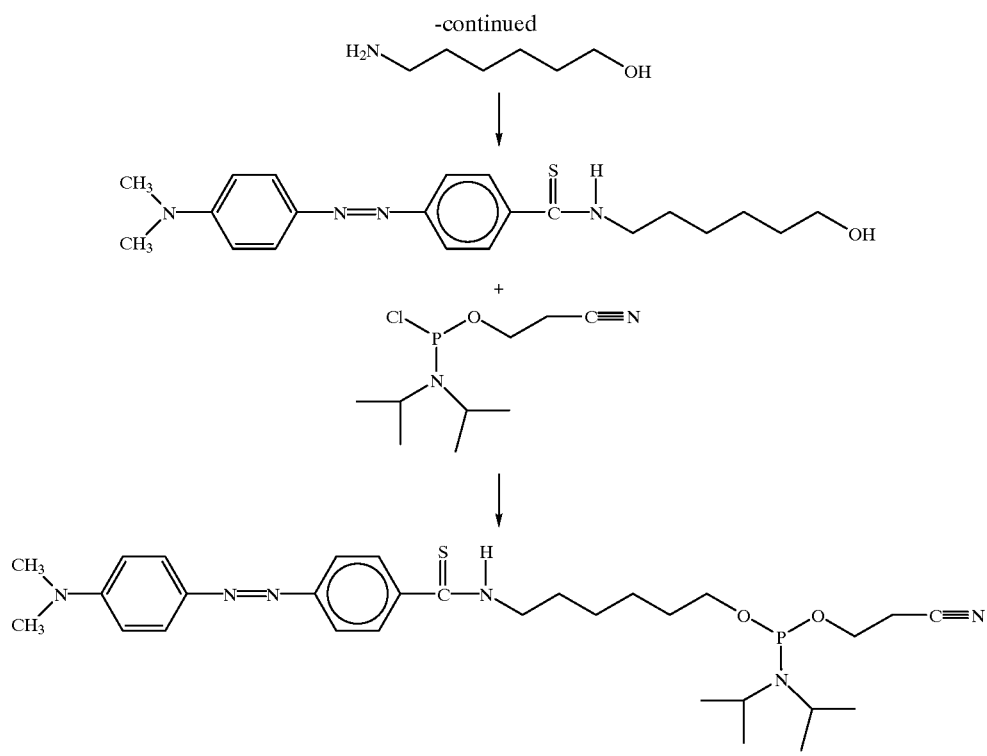

The particulars of each step are as follows. The DABCYL thioamide phosphoramidite may be prepared by reaction of 6-t-butyldimethylsilyloxyhexylamine (i.e., a protected 6-hydroxyhexylamine) with either DABCYL thioamide NHS ester or DABCYL thioamide acid chloride, followed by deprotection of the silyl group to give N-DABCYL thioamide-6-aminohexanol. This is converted to the corresponding cyanoethyl phosphoramidite by the same method as described in the second step in the DABSYL phosphoramidite synthesis recited above.

In general, a solution of DABCYL thioamide NHS ester or DABCYL thioamide acid chloride (Fluka, about 0.2 to 20 gm) is made in about 3 to 300 mL of dry THF (Aldrich) in a flask. To this solution, 6-t-butyidimethylsilyloxyhexylamine (Aldrich, about 0.1 to 10 g) is added drop-wise over approximately 1 to 100 minutes. The solution is stirred under inert gas, preferably argon, overnight at room temperature. Water (about 10 to 1000 mL) and a solvent, such as dichloromethane, (approximately 20 to 2000 mL) are added. The aqueous phase is extracted with more dichloromethane and the combined organic fractions are dried over a hygroscopic agent, filtered, and concentrated in vacua to give a solid. The solid is washed with ethyl acetate/hexane (20:80) and air-dried. At this point, mass spectral data and nuclear magnetic resonance (NMR) data may be obtained on the above-described compound.

The preceding compound (approximately 8 to 800 mg) is dissolved in dry dichloromethane (1 to 100 mL) and stirred. Diisopropylethylamine (0.015 to 1.5 mL) is added by syringe and the mixture is cooled. N,N-Diisopropylchlorophosphoramidite (about 7 to 700 mg) is added slowly as a solution in dry dichloromethane. The reaction mixture is stirred under inert gas for about 5 minutes to 5 hours with warming to room temperature. A solvent, such as methanol, (about 0.1 to 10 mL) is added and the solvent is removed with the use of a rotary evaporator. The resulting oil is extracted several times from aqueous sodium bicarbonate with dichloromethane. The combined organic fractions are dried over a hygroscopic agent and solvent is removed. Flash silica gel chromatography (triethylamine/ethyl acetate/hexane, 6:47:47) is used to obtain the most mobile product as an oil (5 mg). The NMR analysis may be performed on the product.

Methods of Using Labelled Phosphoramidite Compositions

The methods of the present invention also include methods of using the labelled phosphoramidite compositions described herein. The compositions of the present invention are used for 5' labelling of oligonucleotides during chemical synthesis, for example in the phosphoramidite synthetic methods which are well known in the at. The labeled phosphoramidite of the invention is added at the 5' terminus of the oligonucleotide being synthesized, thereby labeling the oligonucleotide. The labeled phosphoramidite may be added to any nucleotide at the 5' terminus. Such labelling of oligonucleotides during chemical synthesis provides benefits over prior art methods of labelling after synthesis as separate post-synthesis labeling reaction steps may be avoided.

Included in the present invention are methods of labelling oligonucleotides with the labelled phosphoramidite compositions, wherein the oligonucleotides are also labelled with fluorogens selected from, but not limited to the group consisting of fluorescein and fluorescein derivatives, phycoerythrin, allo-phycocyanin, phycocyanin, rhodamine, Texas Red, EDANS, BODIPY dyes, tetramethylrhodamine, Cy3 and Cy5. Optimal distances between the labelled phosphoramidite compositions at the 5' terminus and the fluorogen dye depend upon the dye selected, however, the two compositions should be about 5–25 bases apart for quenching, and perhaps more if secondary structures are present.

The labelled oligonucleotides produced by the methods described above may also be used as probes in cloning procedures, blotting procedures such as Northern blot analysis, and hybridization procedures as are well known in the art. Additionally, the labelled oligonucleotides may be used to determine the quality and quantity of DNA and RNA amplification products, also as is known in the art.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. For example, it is to be understood that various amounts of reagents, time, and temperature may be used in the preparation of the labelled phosphoramidite compositions, and in the methods of using them to label oligonucleotides, which may suggest themselves to those skilled in the art without departing from the spirit of the present invention and/or the scope of the appended claims.

EXAMPLE 1

Synthesis of DABSYL Phosphoramidite

This synthesis scheme comprises the steps of first synthesizing a reaction product of DABSYL chloride and 6-aminohexanol, and combining the reaction product with N, N-Diisopropylchloro-β-cyanoethyl-phosphoramidite to produce DABSYL linked to a phosphoramidite (DABSYL phosphoramidite). The particulars of each step are as follows.

A solution of DABSYL chloride (Fluka, 2 g, 6.2 mmole) in 30 mL of dry tetrahydrofuran (THF, Aldrich) was prepared in a round bottom flask. To this solution, 6-amino-1-hexanol (Aldrich, 1 g) was added drop-wise over 10 minutes. The deep red solution was stirred under argon overnight at room temperature. Water (100 mL) and dichloromethane (200 mL) were added. The aqueous phase was extracted with more dichloromethane and the combined organic fractions were dried over $MgSO_4$, filtered, and concentrated in vacuo to give a dark red solid. The solid was washed with ethyl acetate/hexane (20:80) and air-dried to yield 2.0 g (80%). (TLC: ethyl acetate/hexane (1:1) Rf 0.15). The mass spectral data on the above-described compound was as follows: FB+ (nitrobenzyl alcohol) MH+405. Additionally, the nuclear magnetic resonance (NMR) data were as follows: III (CDCl) ppm 7.90 (m, 6H) 6.74 (s, 2H) 3.58 (t, 2H) 3.11 (dd, 1OH) 1.80 (bs, 1H) 1.47, 1.28 (dt, 6H); $^{13}C$ (CDCl) ppm. 162.2, 155.6, 153.2, 143.5, 141.5, 139.5, 127.8, 125.3, 122.5, 111.4, 52.5, 43.1, 40.2, 32.4, 28.4, 26.1, 24.1.

The preceding compound (80 mg, 0.2 mmole) was dissolved in dry dichloromethane (10 mL) in a round bottom flask equipped with a stir bar. Diisopropylethylamine (0.15 mL, 1.0 mmole) was added by syringe and the mixture was cooled with an ice bath. N,N-Diisopropylchlorophosphoramidite (70 mg, 0.3 mmole) was added slowly as a solution in dry dichloromethane. The reaction mixture was stirred under argon for 1 hour with warming to room temperature. Methanol (1 mL) was added and solvent was removed with a rotary evaporator. The resulting oil was extracted several times from aqueous sodium bicarbonate with dichloromethane. The combined organic fractions were dried over $MgSO_4$ and solvent was removed. Flash silica gel chromatography (triethylamine/ ethyl acetate/hexane, 6:47:47) was used to obtain the most mobile product as an oil (5 mg). The NMR data was as follows: 1H (CDCl) ppm 7.89–7.94 (m), 7.20–7.26 (m), 6.74 (d) 3.49 (t, 2H) 3.12 (s, 6H), 2.98–3.07 (m), 1.21–1.60 (m), 0.01 (d, 12H); 13C (CDCl) ppm. 162.3, 155.0, 153.2, 144.0, 140.0. 128.1, 125.7, 122.6, 111.5, 60.0, 47.5, 46.2, 44.8, 43.2, 40.3, 32.3, 29.7, 26.3, 25.8, 24.7, 22.5, 19.4, 1.0.

EXAMPLE 2

Synthesis of DABCYL Phosphoramidite

This synthesis scheme comprises the steps of first synthesizing a reaction product of DABCYL NHS ester or DABCYL chloride and a protected 6-hydroxyhexylamine, deprotecting the reaction product and combining it with N, N-Diisopropylchloro-β-cyanoethyl-phosphoramidite to produce DABCYL linked to a phosphoramidite (N-(4-(4'-dimethylamio-phenyl-azo)-phenyl-carbonyl)-6-aminohexanol N, N-Diisopropylchloro-β-cyanoethyl-phosphoramidite; DABCYL phosphoramidite). The particulars of each step are as follows.

6-t-butyidimethylsilyloxy-hexylamine (i.e., a protected 6-hydroxyhexylamine) was reacted with either DABCYL NHS ester or DABCYL acid chloride, followed by de-protection of the silyl group to give N-DABCYL-6-aminohexanol.

The preceding compound (80 mg, 0.2 mmole) was dissolved in dry dichloromethane (10 mL) in a round bottom flask equipped with a stir bar. Diisopropylethylamine (0.15 mL, 1.0 mmole) was added by syringe and the mixture cooled with an ice bath. N,N-Diisopropylchlorophosphoramidite (70 mg, 0.3 mmole) was added slowly as a solution in dry dichloromethane. The reaction mixture was stirred under argon for one hour with warming to room temperature. Methanol (1 mL) was added and solvent is then removed with a rotary evaporator. The resulting oil was extracted several times from aqueous sodium bicarbonate with dichloromethane. The combined organic fractions were dried over $MgSO_4$ and solvent was removed. Flash silica gel chromatography (triethylamine/ ethyl acetate/hexane, 6:47:47) was used to obtain the most mobile product as an oil.

EXAMPLE 3

Synthesis of DABCYL Thioamide Phosphoramidite

This synthesis scheme, comprises the steps of first synthesizing a reaction product of DABCYL thioamide NHS ester or acid chloride and a protected 6-hydroxyhexylamine, deprotecting the reaction product and combining it with N, N-Diisopropylchloro-β-cyanoethyl-phosphoramidite to produce DABCYL thioamide linked to a phosphoramidite (N-(4-(4'-dimethylamino-phenyl-azo)-phenyl-thio-carbonyl)-6-aminohexanol N, N-Diisopropylchloro-p-cyanoethyl-phosphoramidite; DABCYL thioamide phosphoramidite). The particulars of each step are as follows.

As for DABCYL phosphoramidite, DABCYL thioamide NHS ester or DABCYL thioamide acid chloride is reacted with a protected 6-hydroxyhexylamine (e.g., 6-t-butyidimethylsilyloxyhexylamine), followed by deprotection of the silyl group to give N-(4-(4'-dimethylamino-phenyl-azo)-phenyl-thio-carbonyl)-6-aminohexanol.

The preceding compound (80 mg, 0.2 mmole) was dissolved in dry dichloromethane (10 mL) in a round bottom flask equipped with a stir bar. Diisopropylethylamine (0.15 mL, 1.0 mmole) was added by syringe and the mixture was cooled with an ice bath. N,N-Diisopropylchlorophosphoramidite (70 mg, 0.3 mmole) was added slowly as a solution in dry dichloromethane. The reaction mixture was stirred under argon for 1 hour with warming to room temperature. Methanol (1 mL) was added and solvent is then removed with a rotary evaporator. The resulting oil was extracted several times from aqueous sodium bicarbonate with dichloromethane. The combined organic fractions were dried over $MgSO_4$ and solvent was removed. Flash silica gel chromatography (triethylamine/ethyl acetate/hexane, 6:47:47) was used to obtain the most mobile product as an oil.

EXAMPLE 4

Labelling of Oligonucleotides with Labelled Phosphoramidite Compositions

Oligodeoxynucleotides are prepared on a 1.0 μmole scale using an ABI 380B automated DNA synthesizer using standard reagents supplied by the manufacturer (Applied Biosystems Division of Perkin Elmer, Foster City, Calif.). Oligonucleotide sequences are synthesized from the 3' end using standard phosphoramidite coupling chemistry.

Approximately 50 mg of DABSYL phosphoramidite, DABCYL phosphoramidite or DABCYL thioamide phosphoramidite is dissolved in 1.0 mL solvent such as acetonitrile in a small bottle. Enough solution for 2–3 syntheses on the 1.0 μmole scale is added to a reagent port on the DNA/RNA synthesizer in a procedure similar to that used for the standard base phosphoramidite reagents. This coupling step is added during a DNA or RNA synthesis such that the DABSYL, DABCYL or DABCYL thioamide phosphoramidite labels the last base at the 5' end of the sequence.

The crude oligonucleotides are then de-protected by treatment with ammonium hydroxide for about 4 to 8 hours at about 55° C. The de-protected mixtures are filtered and the solvent is evaporated from the filtrate with a centrifugal vacuum apparatus. Following de-protection, the crude labelled oligonucleotides are analyzed and purified on a Waters Delta Pak 300 A C18 3.9×150 mm reverse phase column using linear gradients over 30 minutes followed by 20 minutes re-equilibration. A linear gradient begins with approximately 90% 50 mM TEAA (triethylammonium acetate)/10% acetonitrile over 30 minutes and ends with approximately 50% 50 mM TEAA/50% acetonitrile. The identity of the conjugated material is confirmed by comparing peak intensities at about 260 nm for DNA and about 260 nm for RNA and the respective peak absorbance for the dye (approximately 450 to 460 nm for DABSYL). Fractions of pure dye-labelled oligonucleotides are pooled and concentrations are determined using the DNA absorbance at 260 nm, or the RNA absorbance at 260 nm, corrected for the respective dye absorbance at that wavelength.

The invention has been described in detail with particular reference to certain embodiments, but variations and modifications can be made without departing from the spirit and the scope of the present invention as defined in the appended claims.

What is clamed is:

1. A composition comprising:

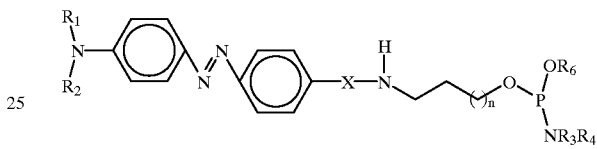

wherein X is $SO_2$, CO, or CS; $R_1$ and $R_2$ are the same or different and are an alkyl group from 1 to 6 carbons in length or can jointly form with N to form a 5 or 6-membered cyclic ring, wherein the ring optionally contains oxygen; $R_3$ and $R_4$ are the same or different, and are an alkyl group from 1 to 10 carbons in length, or isopropyl; n is an integer from 1 to 10, and $R_6$ is $(CH_2)_2CN$ or $CH_3$.

2. The composition of claim 1, comprising:

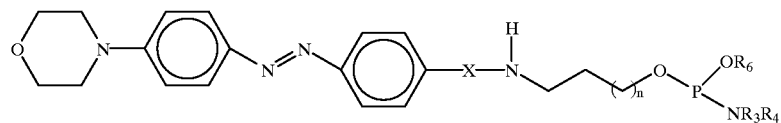

3. The composition of claim 1, selected from the group consisting of:

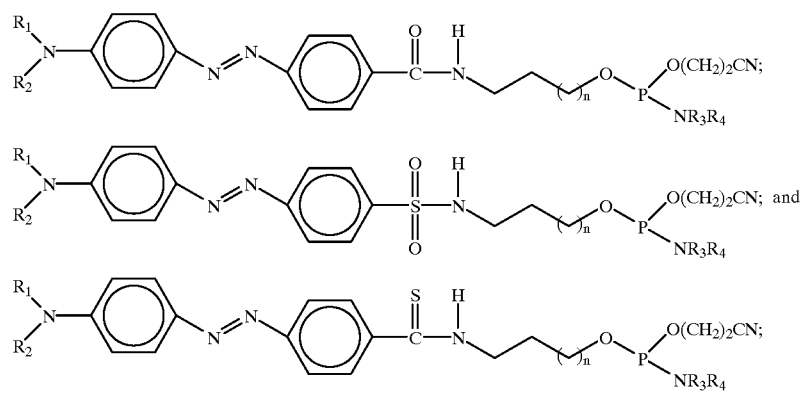

wherein R₁ and R₂ are the same or different and are an alkyl group from 1 to 6 carbons in length or can jointly form with N a 5 or 6-membered cyclic ring, wherein the ring optionally contains oxygen; R₃ and R₄ are the same or different and are isopropyl or an alkyl group from 1 to 10 carbons in length; and n is an integer from 1 to 10.

4. The composition of claim 1, wherein X is SO₂, R₁ and R₂ are the same or different and are methyl or ethyl, R₃ and R₄ are isopropyl and n is an integer from 2 to 8.

5. The composition of claim 1, wherein X is SO₂, R₁ and R₂ are the same or different and are methyl or ethyl, R₃ and R₄ are isopropyl and n is 4.

6. The composition of claim 1, wherein X is CO, R₁ and R₂ are the same or different and are methyl or ethyl, R₃ and R₄ are isopropyl and n is an integer from 2 to 8.

7. The composition of claim 1, wherein X is CO, R₁ and R₂ are the same or different and are methyl or ethyl, R₃ and R₄ are isopropyl and n is 4.

8. The composition of claim 1, wherein X is CS, R₁ and R₂ are the same or different and are methyl or ethyl, R₃ and R₄ are isopropyl and n is an integer from 2 to 8.

9. The composition of claim 1, wherein X is CS, R₁ and R₂ are the same or different and are methyl or ethyl, R₃ and R₄ are isopropyl and n is 4.

10. The composition of claim 7 comprising

13. A method of preparing a labelled phosphoramidite composition comprising the steps of:
 a) reacting DABSYL, DABCYL thioamide or DABCYL with an amino-containing alkyl alcohol to produce a reaction product; and
 b) reacting the reaction product with a phosphoramidite to produce a labelled phosphoramidite composition.

14. The method of claim 13 wherein the label is DABSYL, DABCYL thioamide or DABCYL.

15. The method of claim 13 wherein the amino-containing alkyl alcohol is 6-amino-l-hexanol.

16. The method of claim 13 wherein the phosphoramidite is N, N-Diisopropylchloro-β-cyanoethyl-phosphoramidite.

17. A method of preparing a labelled phosphoramidite composition comprising the steps of:
 a) reacting a label, wherein the label is DABSYL, DABCYL thioamide or DABSYL, with 6-amino-l-hexanol to produce a reaction product; and
 b) reacting the reaction product with a N, N-Diisopropylchloro-β-cyanoethyl-phosphoramidite to produce a labelled phosphoramidite composition.

18. A method of preparing labelled oligonucleotides using the labelled phosphoramidite composition of claim 1, comprising the steps of:
 a) synthesizing an oligonucleotide from a 3' end of the oligonucleotide;
 b) adding the labelled phosphoramidite to the oligonucleotide when a last base is added to a 5' end of the oligonucleotide;

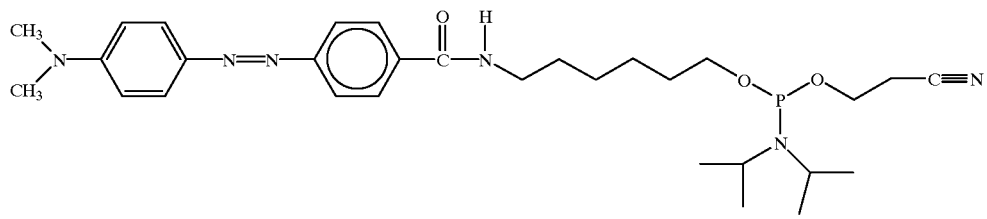

11. The composition of claim 5 comprising

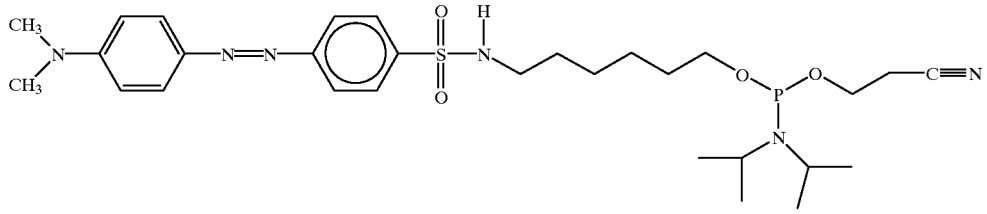

12. The composition of claim 9 comprising

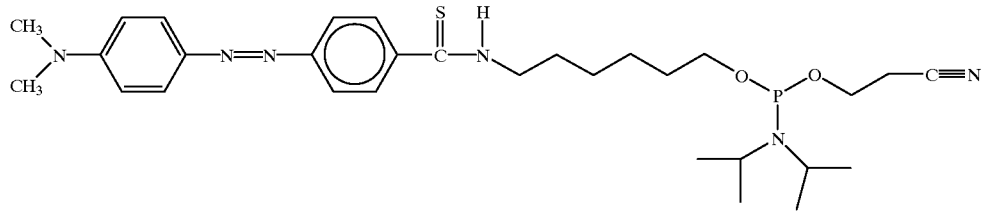

c) de-protecting the oligonucleotide to form a deprotected product; and
d) recovering the deprotected product.

19. The method of claim 18, wherein the labelled phosphoramidite composition is

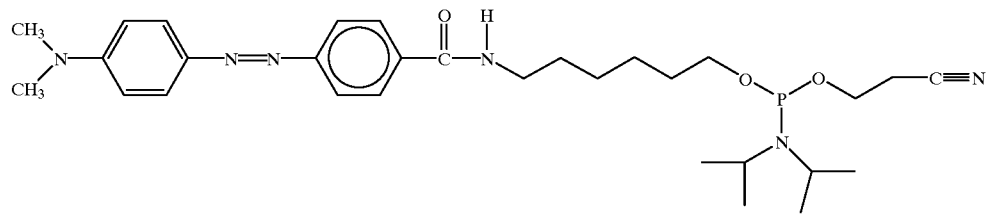

20. The method of claim 18, wherein the labelled phosphoramidite composition is

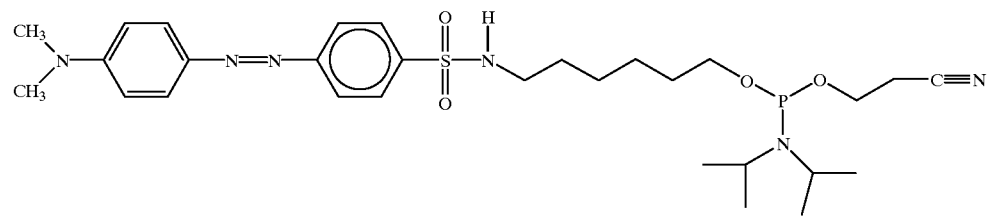

21. The method of claim 18, wherein the labelled phosphoramidite composition is

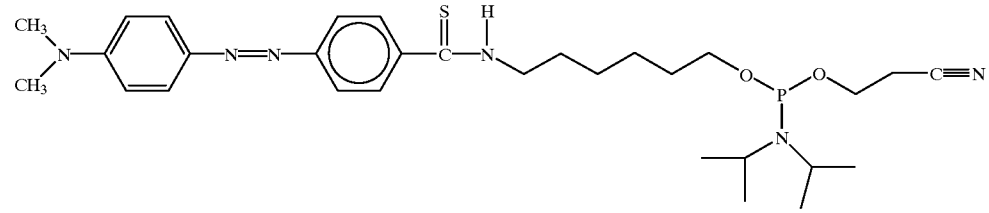

22. A method for detecting a target nucleic acid comprising the step of hybridizing to the target nucleic acid a probe labelled at a 5' end with a composition according to claim 1.

* * * * *